United States Patent [19]

Tsuruoka et al.

[11] Patent Number: 4,991,153

[45] Date of Patent: Feb. 5, 1991

[54] VIBRATION TYPE TRANSDUCER

[75] Inventors: Michihiko Tsuruoka; Wataru Nakagama; Naohiro Kounosu, all of Kanagawa, Japan

[73] Assignee: Fuji Electric Co., Ltd., Kanagawa, Japan

[21] Appl. No.: 326,431

[22] Filed: Mar. 20, 1989

Related U.S. Application Data

[63] Continuation of Ser. No. 129,308, Dec. 7, 1987, abandoned.

[30] Foreign Application Priority Data

Dec. 17, 1986 [JP] Japan .................................. 61-300273
Apr. 24, 1987 [JP] Japan .................................. 62-101624

[51] Int. Cl.$^5$ ...................... H01L 41/04; H01L 41/08
[52] U.S. Cl. .................................... 367/172; 367/167; 367/171; 310/348; 73/702; 73/704
[58] Field of Search ............... 367/141, 157, 165, 166, 367/167, 171, 172, 180; 310/323, 338, 800, 348, 353; 73/702, 708, 721, 727, 737, 756, 861.18, 861.21, 861.31, 861.47, 704

[56] References Cited

U.S. PATENT DOCUMENTS

| | | | |
|---|---|---|---|
| 3,788,140 | 1/1974 | Turtle | 73/861.28 |
| 3,817,098 | 6/1974 | Brown | 73/861.28 |
| 4,208,737 | 6/1990 | Thompson et al. | 367/171 |
| 4,236,235 | 11/1980 | Gilbert | 367/157 |
| 4,600,855 | 7/1986 | Strachan | 310/338 |
| 4,803,671 | 2/1989 | Rochling et al. | 310/800 |

FOREIGN PATENT DOCUMENTS

| | | |
|---|---|---|
| 0087612 | 9/1983 | European Pat. Off. . |
| 0128737 | 12/1984 | European Pat. Off. . |
| 62-98233 | 6/1987 | Japan . |
| 2087558 | 5/1982 | United Kingdom . |

Primary Examiner—Brian S. Steinberger
Attorney, Agent, or Firm—Finnegan, Henderson, Farabow, Garrett, and Dunner

[57] ABSTRACT

The apparatus of the present invention detects the resonant frequency of a vibratory member in contact with a fluid. The detection of the resonant frequency enables the device to be used to detect the density of a fluid which it is in contact with and thereby calculate the flow rate of the fluid. The vibratory member is mounted in a housing in such a way that the chambers on either side of the vibratory member have equal volumes. The fluid enters the device through a conduit and then divides into two equal tubes on either side of an extension of a vibratory member extending down these tubes. The apparatus for measuring the resonant frequency of the vibratory member is mounted on the vibratory member and is comprised of a piezoelectric element coupled to a driver circuit in a feedback loop.

6 Claims, 5 Drawing Sheets

FIG. 4
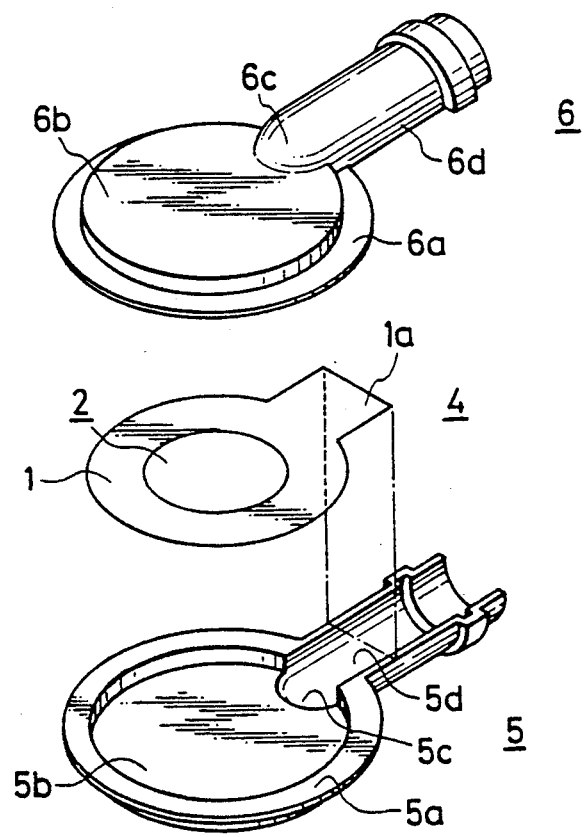
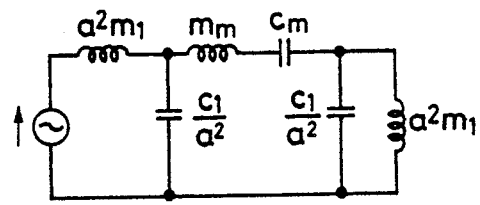
FIG. 5 (A)
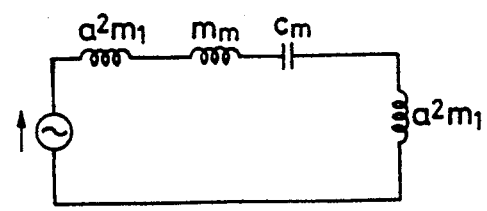
FIG. 5 (B)

4,991,153

VIBRATION TYPE TRANSDUCER

This application is a continuation, of application Ser. No. 07/129,308, filed 12/7/87 now abandoned.

BACKGROUND OF THE INVENTION

The present invention generally relates to a vibration type transducer for measuring a density or a pressure of a fluid brought into contact with a mechanical vibratory member by detecting a resonant frequency of a vibration system including the mechanical vibratory member, and more particularly, to a structure of a transducer suitable for measuring the density or the pressure of the fluid flowing through a conduit line.

The present applicant has proposed a type of transducer (see Japanese Patent Publication No. 239228/1985) composed of a vibratory member, a cavity formed above at least one surface of the vibratory member so as to be opposite this surface and a tube for leading a fluid to be measured into this cavity, this transducer serving to measure the mass, i.e., the density, of the fluid within the tube on the basis of a variation in resonant frequency of a mechanical/acoustic vibration system consisting of the vibratory member, the cavity and the fluid existing in the tube.

The vibration type transducer of this kind is, however, attended with the following characteristics. In the case of measuring the density of the fluid flowing in the conduit line or the like, exciting forces with a wide range of frequencies act on the vibratory member due to deviation of a flow or disturbances of pressure such as a swirl or the like generated in the tube. As a result of this, an oscillation frequency loses stability, and the error in measurement is thereby increased. For this reason, a measuring limit of the above-described transducer comes to a flow-velocity of several m/sec at the most. The measurement is impossible in a range of higher flow-velocities beyond the foregoing limit.

SUMMARY OF THE INVENTION

Accordingly, it is a primary object of the present invention which obviates the above-described characteristics inherent in prior vibration type transducers to provide an improved vibration type transducer which creates a much smaller error in measurement over a wide range of flow-velocities.

To accomplish the above-mentioned object, the transducer according to the present invention is arranged in such a way that: acoustic tubes serving as conduits for leading a fluid to be measured into cavities positioned opposite to individual surfaces of a mechanical vibratory member are provided on both sides of the mechanical vibratory member; dimensions of the cavities are set to be substantially equal to those of the acoustic tubes; the two acoustic tubes are combined; tips of the thus combined tubes are connected to a third conduit to be put in the fluid flowing through the third conduit.

The transducer according to the present invention is further arranged such that at least two cavities positioned opposite to the individual surfaces of the mechanical vibratory member and at least two acoustic tubes serving as the conduits for leading the fluid to be measured into the cavities communicating with the acoustic tubes are provided on both sides of the mechanical vibratory member; the dimensions of the cavities are set to be substantially equal to those of the acoustic tubes provided on the surface and on the underside of the vibratory member, the acoustic tubes are combined; and each tip of the thus combined tubes is connected to one conduit.

To achieve the objects and in accordance with the purpose of the invention, as embodied and broadly described herein, the apparatus for detecting the resonant frequency of a vibratory member in contact with a fluid comprises a housing having an interior chamber, a substantially planar vibratory member mounted in the housing, the vibratory member having opposite first and second sides and disposed in the interior chamber of the housing to define a first and second internal chamber portion, each having substantially the same volume, means integral with the housing for establishing equal flow communication between the fluid in contact with the first and second sides and resonant frequency detection means responsive to the fluid contact and associated with the vibratory member for detecting the resonant frequency of the vibratory member.

The accompanying drawings, which are incorporated in and constitute a part of this specification, illustrate one embodiment of the invention and, together with the description, serve to explain the principles of the invention.

BRIEF DESCRIpTION OF THE DRAWINGS

An embodiment of the present invention will hereinafter be described in detail with reference to the accompanying drawings.

FIG. 4 is an exploded perspective view of FIG. 1.

FIGS. 5A and 5B are equivalent electric circuit diagrams of a vibration system depicted in FIG. 2.

DESCRIPTION OF THE PREFERRED EMBODIMENTS

Figure 1:
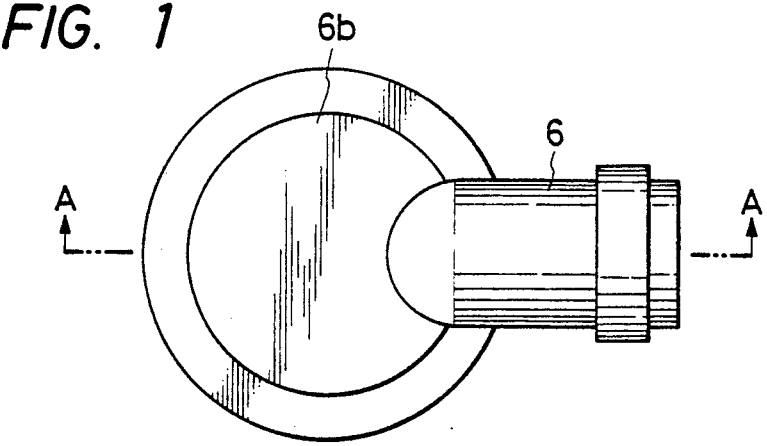
FIG. 1 is a view illustrating an outline of one embodiment of the present invention.
Figure 2:
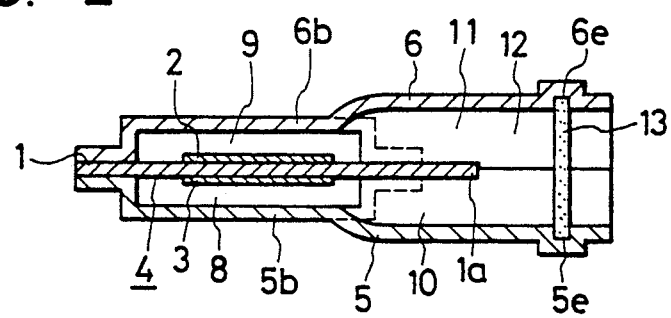
FIG. 2 is a sectional view taken substantially along the line A—A of FIG. 1.
Figure 3:
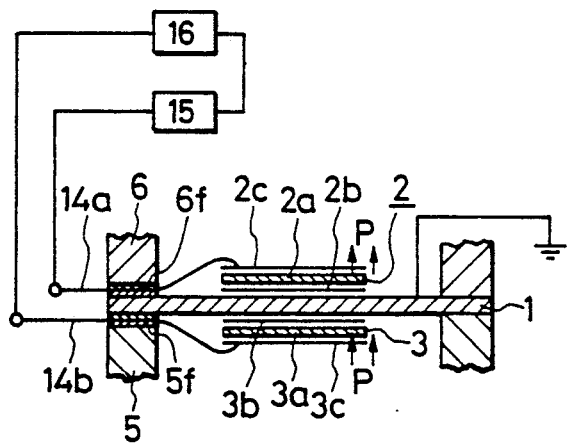
FIG. 3 is a detailed view illustrating the vibratory system of FIG. 2.

In the FIGS. 1–6, the reference numeral 1 denotes a circular substrate including both surfaces to which piezoelectric vibrators 2 and 3 are joined thereto. This substrate 1 is provided with a projection 1a jutting out in the radial direction. The substrate 1 is formed of a metal thin plate such as Kovar or a Ni-Fe alloy, the substrate 1 having a thickness of approximately 0.1 mm and substantially the same coefficient of thermal expansion as that of the piezoelectric vibrators 2 and 3. As fully illustrated in FIG. 3, the piezoelectric vibrator 2 is composed of a disk-like piezoelectric substrate 2a made from a material of a PZT system and of first and second electrodes 2b and 2c which are provided on both surfaces of the substrate 2a. The piezoelectric vibrator 3 consists of a disk-like piezoelectric substrate 3a formed from the same material as that of the substrate 2a and with the same dimensions as those thereof, a first electrode 3b formed on one surface of the substrate 3a and a second electrode 3c formed on the opposite surface thereof. The piezoelectric vibrators 2 and 3 are fixed to the substrate 1 so that the first electrodes 2b and 3b are conductively connected to the substrate 1. The piezoelectric vibrators 2 and 3 are also polarized in the direction indicated by an arrowhead P. The substrate 1 and the piezoelectric vibrators 2 and 3 are combined to form a vibrator generally indicated at 4.

The numeral 5 designates a first cylindrical bottomed housing including a collar 5a provided at its opening end A recess 5c is formed in a part of the bottom 5b, and a groove 5d assuming a semicircular configuration in section is formed to extend from the recess 5c in the radial direction. The numeral 6 represents a second housing assuming substantially the same configuration as that of the first housing 5. As in the case of first housing 5, the second housing 6 has a collar 6a provided at its opening end and a groove 6d formed to extend from a portion 6c of the bottom 6b in the radial direction.

Substrate 1 of vibrator 4 is formed in substantially the same shape as that of each opening end of housings 5 and 6. The projection 1a is sandwiched in between grooves 5d and 6d and extends to partially cover the grooves 5d and 6d in the longitudinal direction thereof. The circumference of the substrate 1 is interposed between the collars 5a and 5b of the first and second housing 5 and 6 and is then hermetically fastened with a screw which is not illustrated. It is to be noted that the first and second housing 5 and 6 are made from materials having the same coefficient of thermal expansion as that of the piezoelectric vibrators 2 and 3.

First housing 5, vibrator 4 and the second housing 6 are laminated sequentially on each other, thereby forming annular cavities 8 and 9 each having the nearly the same volume V between one surface of the vibrator 4 and the bottom 5b of the first housing 5 and between the other surface of the vibrator 4 and the bottom 6b of the second housing 6. On both sides of the projection 1a of the substrate 1 are formed an acoustic tube 10 taking a semiannular shape in section which is surrounded by the first housing 5 and by the projection 1a and an acoustic tube 11 assuming the same configuration which is surrounded by the second housing 6 and by the projection 1a. Ends of acoustic tubes 10 and 11 communicate with a conduit 12 formed from grooves 5d and 6d of first and second housings 5 and 6. The numeral 13 refers to a filter 13 supportably interposed between semiannular grooves 5e and 6e formed in the above-mentioned grooves 5d and 6d. Lead wires generally indicated at 14a and 14b originate at electrodes 2c and 3c of the piezoelectric vibrators 2 and 3, pass through grooves 5f and 6f are sealed by an adhesive agent. The numeral 15 denotes an amplifier 15 for sending an AC voltage through electrodes 2b and 2c on the piezoelectric vibrator 2, and reference numeral 16 designates a feedback circuit 16 for feeding the voltage generated in the piezoelectric vibrator 3 via the electrode 3c back to the amplifier 15.

In the above-described construction, a mechanical/ consisting of the vibrator 4, the cavities 8 and 9 and the acoustic tubes 10 and 11 is expressed in the form of an equivalent electric circuit viewed from the mechanical system. This is illustrated in FIG. 5A, where $m_m$ is the mass of the vibrator 4, $c_m$ is the compliance of the vibrator 4, $m_l$ is the inertance of each of the acoustic tubes 10 and 11, $c_l$ is the acoustic capacity of each of the cavities 8 and 9, and a is the coefficient determined by a plane area of the vibrator 4 and by a sectional area of each of the acoustic tubes 10 and 11. In the Figure, the acoustic system can be approximated to that shown in FIG. 5B by sufficiently increasing a resonant frequency of the acoustic system which is determined by the acoustic tubes 10 and 11 while considerably reducing the acoustic capacities of the cavities 8 and 9, and it follows that the resonant frequency of this acoustic system is determined by the compliance of the vibrator 4, the mass of the vibrator 4 and the inertances of the acoustic tubes 10 and 11. Namely, if the resonant frequency is detected, it is possible to detect the density of the fluid.

When the foregoing transducer is placed into the fluid, a pressure in the conduit 12 fluctuates because of a turbulent flow. This fluctuation of pressure is propagated via the cavities 8 and 9 and via the acoustic tubes 10 and 11 which have substantially the same dimensions to the surface and the under side of the vibrator 4. As a result, there is almost no difference in phase, and it is feasible to prevent a variation in oscillation frequency which is caused by deformation due to imbalance of pressure on the top surface and the underside and further to perform the measurement with minimal error. As is obvious from the description given above, the present invention provides an additional advantage of performing the measurement with high accuracy even if the pressure sharply fluctuates. The fluids within the acoustic tubes 10 and 11 vibrate in antiphase, and hence a so-called closed system in which there is less emission of the acoustic pressure to the outside is created. Moreover, there is almost no influence exerted by outside acoustic impedance associated with the surrounding obstacles. For this purpose, it is of importance to give a specified length to the conduit 12 to which the acoustic tubes 10 and 11 converge With this arrangement, it is possible to obtain the properties which do not depend on the presence of the filter 13.

Figure 6:
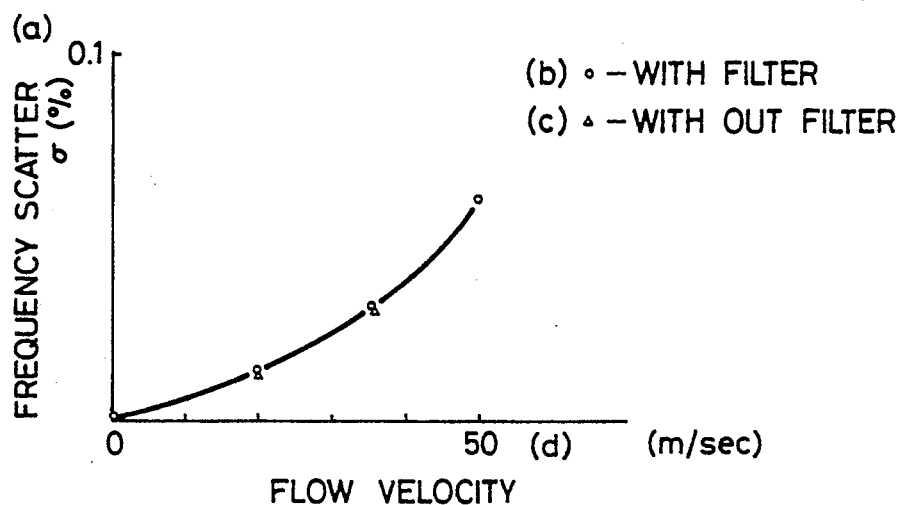
FIG. 6 is a graph showing one example of flow-velocity/frequency scattering characteristics.
Figure 7:
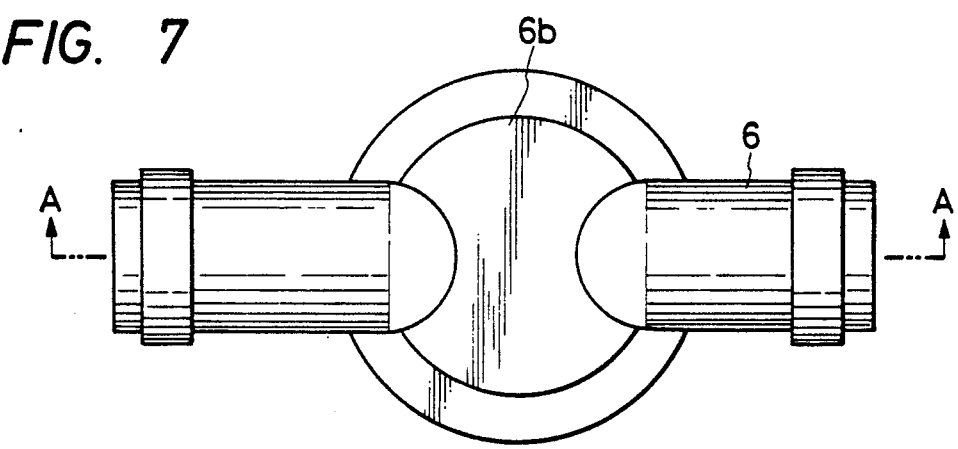
FIG. 7 is a top view of another embodiment of the present invention.
Figure 8:
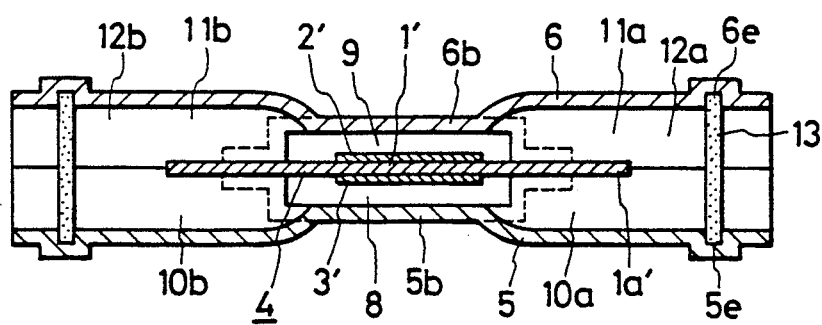
FIG. 8 is a sectional view taken substantially along the line A—A of FIG. 7.
Figure 9:
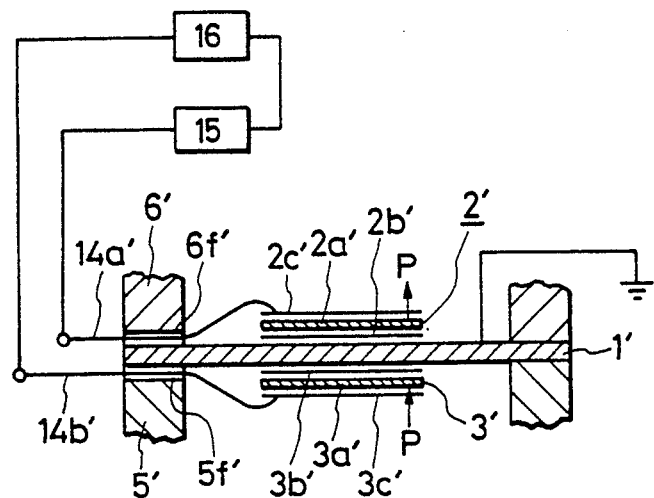
FIG. 9 is a detail view of FIG. 2 illustrating the vibrating system.
Figure 10:
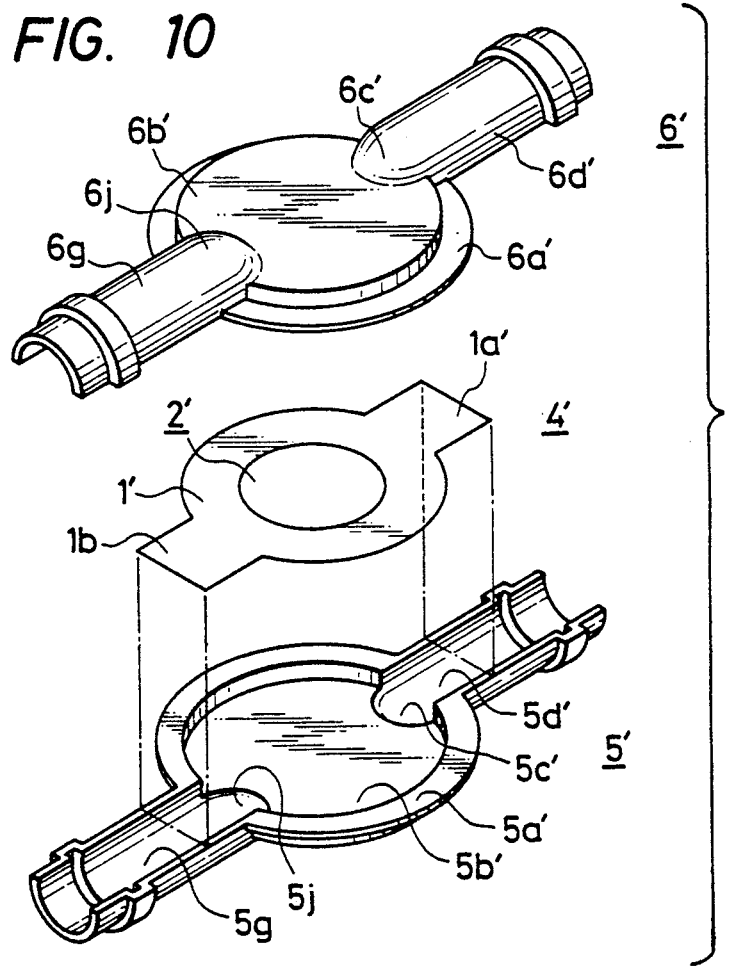
FIG. 10 is an exploded perspective view of FIG. 7.

FIG. 6 shows data of an experiment for researching influences of a flow-velocity by inserting the transducer into a conduit line having an aperture of 60 $\phi$. It can be understood from these experimental data that a scatter $\sigma$ in frequency exhibits an extremely small rate of 0.1% or less within a range of flow-velocities lower than 50 m/sec.; a mean value occurs after a loss of pressure in the conduit line; and favorable characteristics are shown.

In FIGS. 7–11, the numeral 1' denotes a circular substrate having piezoelectric vibrators 2' and 3' are joined to both surfaces. The substrate 1' includes two regions of projection 1a' and 1b each jutting out in the radial direction. The substrate 1' is formed of a thin metal plate such as the Kovar and the Ni-Fe alloy, this substrate 1' having a thickness of approximately 0.1 mm and substantially the same coefficient of thermal expansion as that of the piezoelectric vibrators 2' and 3'. As fully illustrated in FIG. 9, the piezoelectric vibrator 2' consists of a disk-like peizoelectric substrate 2a' made from the material of the PZT system and first and second electrodes 2b' and 2c' provided on both surfaces of the substrate 2a'. The piezoelectric vibrator 3' is composed of a disk-like piezoelectric substrate 3a' formed from the same material as that of the substrate 2' and with the same dimensions as substrate 2a' a first electrode 3b' provided on one surface of the substrate 3a' and a second electrode 3c' provided on the other surface thereof. The piezoelectric vibrators 2' and 3' are fixed to the substrate 1' so that the first electrodes 2b' and 3b' are conductively connected to the substrate 1'. The piezoelectric vibrators 2' and 3' are polarized in the direction indicated by an arrowhead P. A vibrator 4' generally indicated at reference numeral 4' is comprised of substrate 1' and piezoelectric vibrators 2' and 3'.

The numeral 5' stands for the first cylindrical bottomed housing including a collar 5a' provided at its opening end. Recesses 5c' and 5j are formed in part of a bottom 5b'. Grooves 5d' and 5g are formed in part of the bottom 5b'. Grooves 5d' and 5g each assuming a semicircular cross-sectional configuration are formed to extend from the recesses 5c' and 5j in the radial direction.

The numeral 6' denotes a second housing 6' assuming substantially the same configuration as that of the first housing 5'. As in the case of the first housing 5', the second housing 5' has a collar 6a' provided its opening end and is formed with grooves 6d' and 6g extending from portions 6c' and 6j of a bottom 6b' in opposite radial directions.

The substrate 1' of the vibrator 4' is formed in substantially the same shape of that of each opening end of housing 5' and 6'. The projections 1a' and 1b sandwiched in between grooves 5d', 6d' and grooves 5g and 6g, respectively, are long enough to partially cover the grooves 5d', 6d', 5g and 6g in the longitudinal direction thereof. The circumference of the substrate 1'' is interposed between the collars 5a' and 6a' of the first and second housings 5' and 6' and is then hermetically fastened with a screw which is not illustrated. It is to be noted that the first and second housings 5' and 6' are shaped from materials having the same coefficient of thermal expansion as that of the peizoelectric vibrators 2' and 3'.

The first housing 5', the vibrator 4' and the second housing 6' are sequentially laminated to each other, thereby forming annular cavities 8' and 9' each having nearly the same volume V' between one surface of the vibrator 4' and the bottom 5b' of first housing 5' and between the other surface of the vibrator 4' and the bottom 6b' of the second housing 6'. On both sides of the projections 1a' and 1b' are formed a pair of acoustic tubes 10a and 10b each having a semicircular cross section which are surrounded by the first housing 5' and by the projections 1a' and 1b' and another pair of acoustic tubes 11a and 11b each having substantially the same configuration as acoustic tubes 10 and 10b and each is surrounded by the second housing 6 and by the projections 1a and 1b. Ends of the two pairs of acoustic tubes 10a, 10b, 11a and 11b communicate with conduits 12a and 12b formed from the grooves 5d' and 6d' of the first and second housings 5' and 6'. The numeral 13 stands for a filter supportedly interposed between semiannular grooves 5e' and 6e' formed in the above-mentioned grooves 5d' and 6d'. Lead wires generally indicated at 14a' and 14b' originate at the second electrodes 2c' and 3c' of the piezoelectric vibrators 2' and 3' and pass through grooves 6f' and 5f' formed in the housings 6' and 5' to the outside. The grooves 6f' and 5f' are sealed by an adhesive agent. The numeral 15' denotes an amplifier for sending an AC voltage through the electrodes 2b' and 2c' on the piezoelectric vibrator 2'; and 16' designates a feedback circuit for feeding the voltage generated in the piezoelectric vibrator 3' via the electrode 3c' back to the amplifier 15'.

Figure 11A:
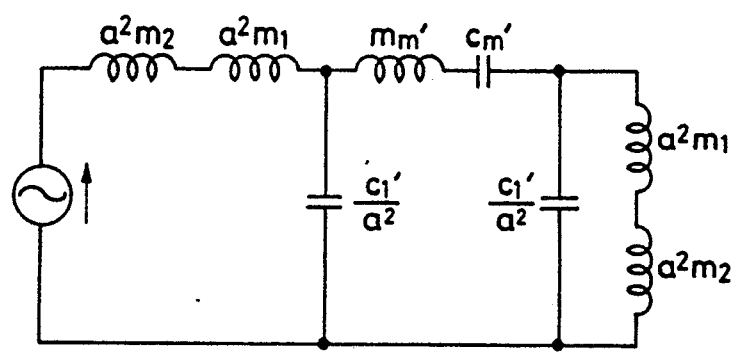
FIGS. 11A and 11B are equivalent electric circuit diagrams of the vibration system shown in FIG. 8.
Figure 11B:
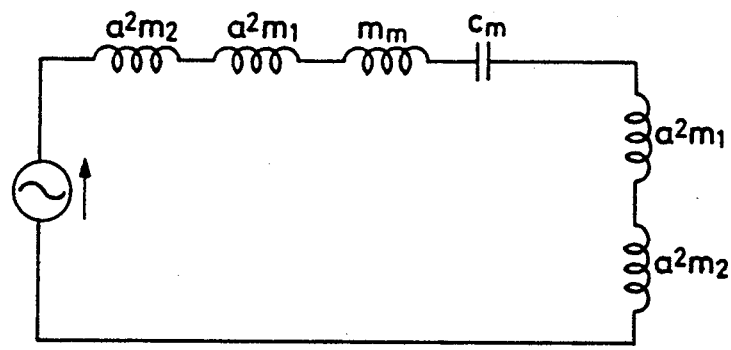

In the above-described construction of the mechanical/acoustic vibration system consisting of the vibrator 4', the cavities 8' and 9' and the acoustic tubes 10a, 10b, 11a, and 11b is expressed in the form of an equivalent electric circuit viewed from the mechanical system. This is illustrated in FIG. 5(A), where $m_m'$ is the mass of the vibrator 4', $c_m'$ is the compliance of the vibrator 4', $m_l$ is the inertance of each of the acoustic tubes 10a, 10b, 11a and 11b, $c_l'$ is the acoustic capacity of each of the cavities 8 and 9, and a' is the coefficient determined by a surface area of the vibrator 4 and by a sectional area of each of the acoustic tubes 10a, 10b, 11a and 11b. In FIG. 11, the acoustic system can approximate the equivalent circuit in FIG. 5(B) by sufficiently increasing a resonant frequency of the acoustic system which is determined by the acoustic tubes 10a, 10b, 11a and 11b while considerably decreasing the acoustic capacities of the cavities 8 and 9, and it follows that the resonant frequency of this system is determined by the compliance of the vibrator 4', the mass of the vibrator 4' and the inertances of the acoustic tubes 10a, 10b, 11a and 11b. If the resonant frequency is detected, it is possible to detect the density of the fluid.

When the above-described transducer is placed into the flowing fluid in such a manner that an axis of the conduits is arranged in parallel with a flow line of the fluid one of two conduits, e.g., a conduit 12b, with the open face of the conduit directed upstream, while the other conduit, e.g., a conduit 12a is directed downstream, the fluid to be measured flows from the acoustic tubes 10b and 11b, through the cavities 8 and 9 and into the acoustic tubes 10a and 11a. The fluids within the acoustic tubes 10a, 10b, 11a, 11b are always replaced, thereby reducing an amount of transfer of heat with respect to the tube walls. In consequence, an error in measurement caused by thermal influences of the wall surfaces of the housing decreases, and it is feasible to perform the measurement with high accuracy for a variation in density of the fluid which is attributed to a sharp change in temperature. The pressures in the conduits 12a and 12b fluctuate because of disturbances in the flow. This fluctuation of pressure is propagated via the cavities 8 and 9 and via the acoustic tubes 10a, 10b, 11a and 11b each having substantially the same dimensions to the top surface and the underside of the vibrator 4. Hence, there is almost no difference in phase, and it is possible to prevent a variation in oscillation frequency which is caused by deformation due to imbalance of pressures on the surface and on the underside and further to perform the measurement with a minimized error. The fluids within the acoustic tubes 10, 10b, 11a and 11b vibrate in antiphase, and hence a so-called closed system in which there is less emission of an acoustic pressure to the outside is created. Moreover, there is almost no influence is exerted by the outside acoustic impedance associated with the surrounding obstacles.

It should be noted that the number of the acoustic tubes connected to the cavities is not necessarily two, but there may be a plurality of tubes on condition that no problems arise due to the split vibration which is derived from a reduction in a fixed area of the vibrator 4. When increasing the number of the acoustic tubes, the fluids in the housing 5 and 6 are replaced not according to the direction in which the fluid flows but invariably to the dynamic pressure of the flow, thereby creating a still smaller error in measurement. If the number of the acoustic tubes is set to a value given by $2n+1$ ($n=1, 2 ...$) in which the split vibration can not easily be caused, more favorable results are obtained.

As is apparent from the description given above, the present invention provides the following effects. The acoustic tubes and the cavities which have substantially the same dimensions are provided on both sides of the vibratory member, and the two lengths of independent acoustic tubes are combined so that the ends thereof are connected to the conduit. In this arrangement, the disturbances of pressure are propagated to the top surface and the underside of the vibratory plate with no difference of phase when there are abrupt fluctuations in pressure of the fluid flowing through the conduit line. It is therefore possible to measure the density with high accuracy by eliminating the variation in frequency which is attributed to the difference between the pressures of the two surfaces of the vibratory plate and further to increase the response time. Since the fluids within the two acoustic tubes vibrate in antiphase with respect to each other, the emission of acoustic pressure to the outside is reduced. As a result, no variation in outside acoustic impedance exerts influence on the device.

According to the present invention, at least two cavities and at least two acoustic tubes are provided on both sides of the vibratory member serve as conduits for the fluid to be measured in the cavities communicating with the above-mentioned acoustic tubes. The dimensions of the cavities and the acoustic tubes are set to be substantially equal on both surfaces of the vibratory member, and the two lengths of acoustic tubes provided on the surface and on the underside of the vibratory member are combined to make one conduit at the end of each of the acoustic tubes. In this embodiment, part of the fluid flowing within the conduit line flows through the conduit into the cavities, thereby speeding up the replacement of the fluids within the housings. The fluids within the acoustic tubes have less transfer of heat with respect to the wall surfaces of the housings. A highly accurate measurement can be carried out for the variation in density of the fluid which is attributed to the sharp change in temperature. The disturbances of pressure are propagated to the top surface and to the underside of the vibratory plate with no difference of phase when there are large fluctuations in pressure in the fluid flowing through the conduit line. It is therefore possible to measure the density with high accuracy by eliminating the variation in frequency which is due to the difference between the pressure on the surface and on the underside of the vibratory plate and further to increase the velocity of response. Since the fluids in the acoustic tubes provided on the surface and on the underside of the vibratory plate vibrate in antiphase with respect to each other, the emission of acoustic pressure to the outside is reduced Consequently, variation in outside acoustic impedance does not affect the device.

It will be apparent to those skilled in the art that various modifications and variations can be made in the apparatus of the present invention without departing from the scope or spirit of the invention. Thus, it is intended that the present invention cover the modifications and variations of this invention provided they come within the scope of the appended claims and their equivalence.

We claim:

1. An apparatus for detecting the resonant frequency of a vibratory member in contact with a fluid, comprising:

a housing having an interior chamber;

a substantially planar vibratory member mounted in said housing, said vibratory member having opposite first and second sides and disposed in said interior chamber of the housing to define a first and second cavity, each of said first and second cavities having substantially the same volume;

means integral with said housing for establishing equal flow communication between the fluid in contact with said first and second sides; and resonant frequency detection means responsive to said fluid contact and operatively coupled to said vibratory member for detecting the resonant frequency of said vibratory member.

2. An apparatus according to claim 1, wherein said housing means includes an annular wall, said wall defining said first and second cavities.

3. An apparatus according to claim 2, wherein said means for establishing flow communication comprises at least one inlet member integrally formed with said housing wherein said inlet member includes:

a first acoustic tube extending radially from said annular housing, said first acoustic tube having an interior defined by an integral extension of said annular housing and an extension of said vibratory member;

a second acoustic tube extending radially from said annular housing and coextensive to said first acoustic tube, said second acoustic tube having an interior defined by an integral extension to said housing and said extension of said vibrating member; and wherein the volume of said first acoustic tube and the volume of said second acoustic tube are substantially equal.

4. An apparatus according to claim 3, wherein said inlet means further includes a conduit portion comprised of the integral extensions of the housing from the end of said extension of said vibratory member to the end of both integral extensions.

5. An apparatus according to claim 4, wherein said means for establishing flow communication include a plurality of said fluid inlet means.

6. An apparatus according to claim 5, wherein the extensions to said housing are arcuate.

* * * * *

UNITED STATES PATENT AND TRADEMARK OFFICE
CERTIFICATE OF CORRECTION

PATENT NO. : 4,991,153
DATED : February 05, 1991
INVENTOR(S) : Michihiko Tsuruoka et al.

It is certified that error appears in the above-identified patent and that said Letters Patent is hereby corrected as shown below:

Title Page, Inventors, Line 2, "Nakagama" should be --Nakagawa--.

Claim 3, Column 8, Line 33, after "housing" insert -- , --.

Signed and Sealed this

Fifth Day of January, 1993

Attest:

DOUGLAS B. COMER

Attesting Officer    Acting Commissioner of Patents and Trademarks